United States Patent [19]

Smith

[11] Patent Number: 4,985,018
[45] Date of Patent: Jan. 15, 1991

[54] CATHETER GRIP

[75] Inventor: Michael F. Smith, Harston, England

[73] Assignee: Cambridge Autotransfusion Service, Cambridge, England

[21] Appl. No.: 310,764

[22] Filed: Feb. 14, 1989

[30] Foreign Application Priority Data

Feb. 15, 1988 [GB] United Kingdom ............... 8803467

[51] Int. Cl.⁵ ............................................. A61M 5/00
[52] U.S. Cl. ................................... 604/161; 604/177
[58] Field of Search ............... 604/177, 178, 159, 160, 604/161, 280

[56] References Cited

U.S. PATENT DOCUMENTS

| 673,598 | 5/1901 | Dolge | 128/345 |
|---|---|---|---|
| 3,589,361 | 6/1971 | Loper | 604/177 |
| 3,677,243 | 7/1972 | Nerz | 604/161 |
| 3,766,915 | 10/1973 | Rychlik | 604/161 |
| 3,910,272 | 10/1975 | Forberg | 604/161 |
| 4,449,973 | 5/1984 | Luther | 604/161 |
| 4,471,778 | 9/1984 | Toye | 604/160 |
| 4,631,059 | 12/1986 | Wolvek et al. | 604/161 |
| 4,687,469 | 8/1987 | Osypka | 604/161 |
| 4,743,265 | 5/1988 | Whitehouse et al. | 604/161 |
| 4,813,929 | 3/1989 | Semrad | 604/161 |

FOREIGN PATENT DOCUMENTS 3140915 5/1982 Fed. Rep. of Germany ...... 604/161

Primary Examiner—John D. Yasko
Assistant Examiner—Anthony M. Gutowski
Attorney, Agent, or Firm—Leydig, Voit & Mayer

[57] ABSTRACT

A catheter grip comprises a pair of members which can be folded about a hinge and pressed lightly together with one hand to hold a catheter firmly, but without damage, in a passage formed by grooves in the members and projecting portions thereof which form a tapered spigot through which the catheter extends. The grip facilitates insertion of a catheter into a vein through a peel sheath and the subsequent removal of the sheath, for which purpose the catheter is held steady by the grip with the tip of the spigot forming a seal in the lumen of the sheath while it is withdrawn over the spigot and thereby split longitudinally along its length.

8 Claims, 2 Drawing Sheets

CATHETER GRIP

BACKGROUND OF THE INVENTION

1. Field of the invention

This invention relates to the insertion of a catheter into a vein or other vessel of the human or animal body via a peel sheath, such as in the insertion of Hickman/-Broviac Long Term Venous catheters, and is particularly concerned with a device for facilitating the catheter insertion and the removal of the peel sheath.

2. Summary of the prior art

In general, the insertion of such catheters is carried out as follows. Firstly, a hollow needle is inserted into the selected vessel, and a flexible guide wire having a non-injuring leading end (known as a Seldinger wire) is pushed into the vessel through the needle. The needle is then removed from the vessel and the guide wire, and a tubular vessel dilator having a tapering leading end is inserted into the vessel to the required position over the guide wire, followed by a thin plastics tube, known as a peel sheath which is a close sliding fit on the vessel dilator. The guide wire and the vessel dilator are then withdrawn from the vessel and the peel sheath so that the catheter can be introduced into the vessel through the peel sheath. Finally, when the catheter has been inserted as required, the peel sheath is removed.

However, since it will often not be possible to withdraw the peel sheath along the whole length of the catheter because the entry point of the catheter into the body may be elsewhere, particularly in the case of a long term deep vein insertion, the peel sheath is designed to be removed by splitting its proximal end and pulling the split portions apart so that the sheath tears or peels in two along its entire length as it is withdrawn from the vessel. The problem with this arrangement is that if two hands are used to pull the sheath apart, as is often necessary, there is a tendency for the catheter to be drawn out of the vessel with the sheath unless someone else holds the catheter in place. Furthermore, in the case of a venous insertion there is often considerable haemorrhage through the sheath, even though the catheter is a close fir within the peek sheath, because of the distortion of the sheath induced by the peeling process and the pressure of the blood in the vein.

SUMMARY OF THE INVENTION

With the aim of overcoming this problem, according to the invention there is provided a catheter grip comprising a pair of members which can be closed together to bracket a catheter and can be held by one hand so that the catheter is held firmly between the members but without damaging the catheter, each member having a portion for co-operating with a portion of the other member to form a spigot of which at least the tip will fit closely around the catheter and within the peel sheath to form a seal between the catheter and the sheath in front of the advancing split as the Sheath S withdrawn and split apart.

In use, the grip will be closed around the catheter after it has been inserted through the peel sheath into the vessel, although if preferred it can be placed in position before the catheter is inserted and used to hold the catheter as it is inserted. When the peel sheath is to be removed, its proximal end is split and the grip, with the catheter held firmly therein, is moved to locate the tip of its spigot portion in the lumen of the sheath immediately beyond the split portions. In this respect, preferably at least the tip of the spigot portion is substantially symmetrical about its axis. Then, with the grip held firmly in one hand to hold the catheter in position, the other hand is used to pull one of the split ends of the sheath in a direction so as to withdraw the sheath from the vessel. In so doing the spigot portion of the grip, which is preferably shaped so that it tapers externally towards its tip, acts to split the sheath along its length as it is withdrawn, while the tip of the spigot seals the sheath immediately upstream of the advancing split and thereby prevents potentially dangerous haemorrhage during the removal process. Once the peel sheath has been removed, the catheter can be adjusted finally in position before releasing the grip and removing it from the catheter.

As will be appreciated, the catheter grip in accordance with the invention will thus enable a catheter to be inserted and the peel sheath to be removed easily and safely by a single person and in a manner which substantially reduces blood loss. In addition, the use of the catheter grip has the advantage that it obviates the need for any of the operating personnel to touch any part of the catheter which is likely to enter the vessel. Although they will be wearing surgical gloves, these may have a light dusting of starch which can act as a clotting agent. The catheter grip will of course be sterilized and will conveniently be provided as part of the sterile catheter insertion pack which is commonly used for such insertions.

Preferably each of the members of the catheter grip has a groove for receiving the catheter when the members are closed together, each groove having a substantially semi-circular cross-sectional profile and extending through the spigot forming portion of the member. Obviously, the grooves will be of a radius which substantially corresponds to the outer diameter of the catheter with which the grip is to be used.

Although the members may be separate from each other, generally it will be preferred for the members to be connected together by a hinge about which the members are folded to the closed position. In this case it will be convenient to form the grip as a single plastics moulding in which the members and the hinge are formed integrally with each other.

If desired, the members of the grip may be provided with locating means which are arranged to interengage to locate and maintain the members correctly positioned relative to each other when they are closed together. For example, such locating means may comprise a locating pin on at least one of the members and a corresponding hole in the other member arranged to receive the locating pin as a tight fit when the members are correctly closed.

A preferred embodiment of the catheter grip in accordance with the invention will now be described, by way of example, with reference to the accompanying drawings.

DESCRIPTION OF THE PREFERRED EMBODIMENT

Figure 1:
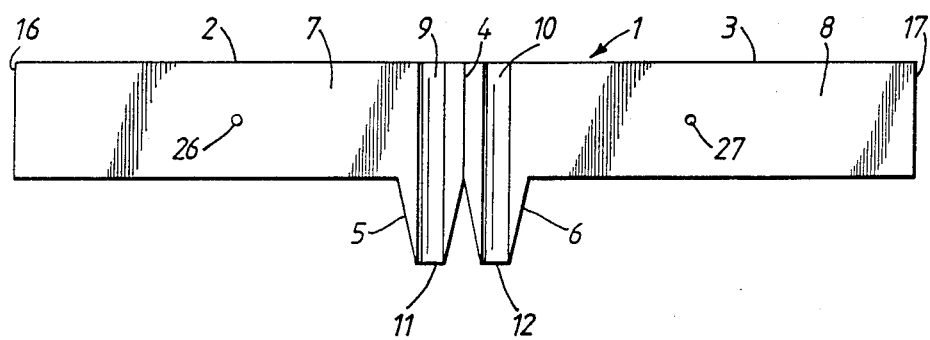
FIG. 1 is a side elevation of the grip in its open position showing the faces of its members which meet when the grip is closed
Figure 2:
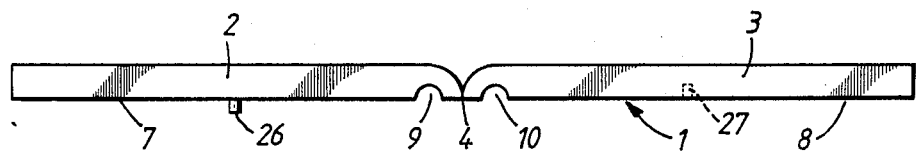
FIG. 2 is a top plan view of the grip in the open position as shown in FIG. 1.
Figure 3:
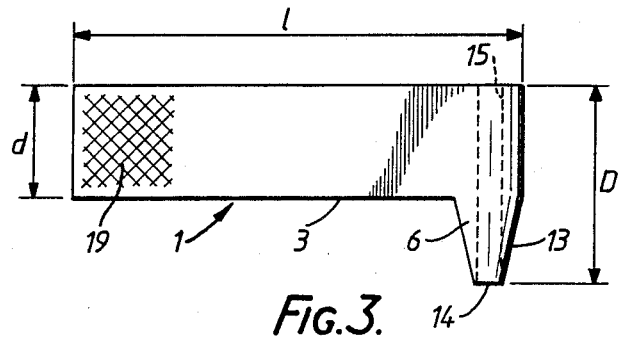
FIG. 3 is a side elevation of the grip in its closed position.
Figure 4:
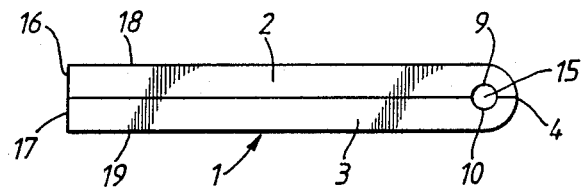
FIG. 4 is a top plan view of the grip in the closed position as shown in FIG. 3; and, FIG. 5 is a diagrammatic view illustrating the grip in operation.

The grip 1 is formed by a one-piece strip moulded from a suitable plastics material to provide a pair of members 2,3 which are separated by an integral flexible hinge portion 4 at the centre of the strip and extending transversely to the longitudinal direction thereof so that the members 2 and 3 can be folded from an open position as shown in FIGS. 1 and 2 to a closed, face-to-face position as shown in FIGS. 3 and 4. The members 2 and 3 are symmetrical about the hinge 4 and each is formed with a portion 5 6 projecting laterally from one of its longitudinally extending edges at a position adjacent the hinge 4 and in the plane of the member.

The meeting faces 7,8 of the members 2,3 are each provided with a groove 9,10 of semi-circular cross-section extending, parallel to the hinge 4, transversely across the member from the longitudinal edge opposite the projecting portion 5,6 to the remote edge 11,12 of the projecting portion. The projecting portions 5 and 6 are shaped so that, when the grip 1 is folded to its closed position, the portions 5,6 co-operate to form a substantially frusto-conical spigot 13 which tapers towards a relatively thin circular tip 14 defined by the edges 11,12 of the projecting portions and symmetrically surrounding one end of a cylindrical passage 15 formed by the meeting grooves 9,10.

As shown, the grooves 9 and 10 are located very much closer to the hinge 4 than to the remote free ends 16,17 of the members 2,3. Thus, when the grip is closed, it may be held near the free edges 16 and 17 well away from, and to one side of, the passage 15 which, in use, holds the catheter. If desired, the outer faces 18,19 of the members 2,3 near the free ends 16,17 may be textured, such as indicated in FIG. 3, or otherwise treated to facilitate the hold on the grip which it is necessary for a person to exert during use. In addition, although not essential, one of the members 2,3 may be provided with a pin projecting from its face 7,8, such as shown at 26 in FIGS. 1 and 2, for location reasonably tightly in a correspondingly positioned hole 27 in the face of the other member when the grip is closed in order to facilitate holding the grip in the correct closed position.

Figure 5:
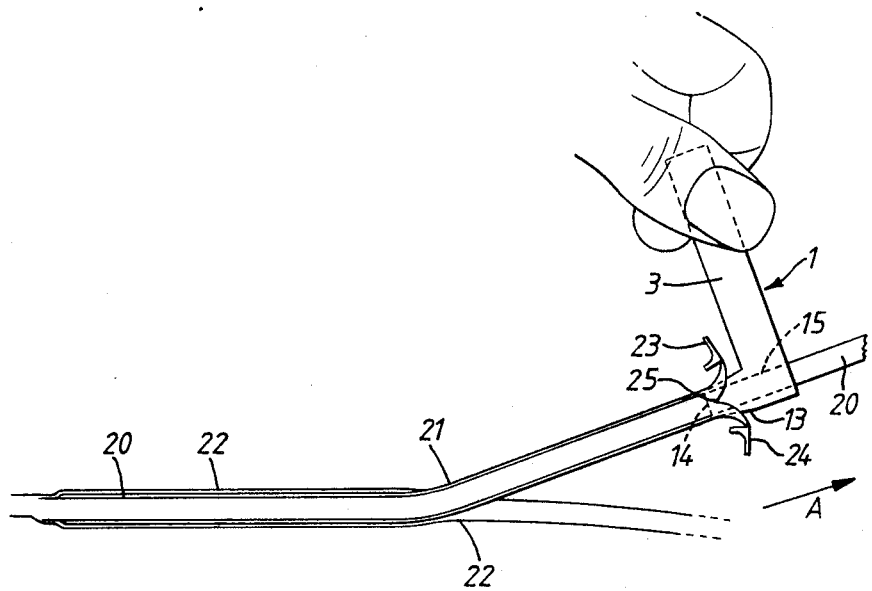

The grip 1 is used as described earlier, and FIG. 5 illustrates the operative position of the grip in relation to a catheter and a peel sheath immediately prior to withdrawal of the sheath. The grip 1 is shown in its closed position with a catheter 20 extending through the passage 15 of the grip and also through a peel sheath 21 into a vein 22. The proximal end of the peel sheath 21 is clamped in a frangible element in a known manner, and when the sheath is to be withdrawn the flangible element is snapped into two parts 23,24 to initiate the longitudinal splitting of the sheath. The grip 1, with the catheter 20 held tightly in the passage 15 by means of finger pressure pressing the members 2 and 3 together, is moved towards the sheath 21 to bring the tip 14 of the spigot portion 13 into a sealing position within the lumen of the sheath 21 just beyond the split 25 as shown. Then, still while holding the catheter 20 firmly in position by means of the grip 1, one of the split ends of the sheath is pulled, by means of the broken part 24 of the frangible element connected thereto, in the general direction of the arrow A to withdraw the sheath from the vessel 22 and the catheter 20. As the sheath is withdrawn it is pulled over the frusto-conical spigot portion 13 of the grip 1 causing the split to advance longitudinally along the sheath at the same rate as it is withdrawn, the tip 14 of the spigot thus maintaining a seal between the sheath and the catheter as the sheath is withdrawn. When withdrawal of the sheath 21 is complete the grip 1 is unfolded and removed from the catheter 20.

As will be appreciated, the radius of the grooves 9,10 will be chosen so that the diameter of the passage 15 formed when the grip is closed is substantially equal to the outer diameter of the catheter 20, so that when the grip is closed and the members 2 and 3 are pressed together the catheter will be lightly clamped and held firmly in position but without damage to the catheter. Slight relaxation of the pressure on the members 2 and 3 will allow the catheter to be pushed through the grip if desired. Apart from the dimensions at the tip 14 of the spigot portion 13, which must be able to fit and seal within the lumen of the sheath 21, the other dimensions of the grip are not critical and may be selected as desired. For example, the length 1 of the closed grip may be about 3.0 cm, the height d at the held end may be about 1.0 cm, and the height D at the catheter end may be about 1.5 cm for a grip intended for use in treating adult patients. For paediatric use, however, the grip may be scaled down to about ⅔rds of this size.

I claim:

1. A catheter grip for use in a method of inserting a catheter employing a peel sheath, said grip comprising first and second members, and single hinge means interconnecting said first and second members whereby said members can be closed together about said hinge means to bracket said catheter and said members can be held by one hand so that said catheter is held firmly between said members but without damaging said catheter, each of said first and second members having a spigot forming portion which cooperates with the respective portion of the other of said members to define a hollow spigot for receiving said catheter therethrough when said members are closed together, said spigot having a tip which is substantially symmetrical about the axis of said spigot, and said spigot being externally tapered to a thin circular edge at said closely around the entire in use, said tip will fit closely around the entire circumference of said catheter and within said peel sheath to form a seal between said catheter and said sheath in front of the advancing split as said sheath is withdrawn and split apart, said hinge means being located between said spigot forming portions.

2. A catheter grip as claimed in claim 1, wherein each of said first and second members has means defining a groove for receiving said catheter when said members are closed together, said groove having a substantially semi-circular cross-sectional profile and extending through said spigot forming portion of said respective member.

3. A catheter grip as claimed in claim 2, wherein said first and second members and said hinge means are formed integrally as a single plastics moulding.

4. A catheter grip as claimed in claim 3, wherein said groove of each of said first and second members is located very much closer to said hinge means than to the opposite free edge of said respective member.

5. A catheter grip as claimed in claim 4, wherein said groove of each of said first and second members is parallel to said hinge means.

6. A catheter grip as claimed in claim 2, wherein said first and second members are symmetrical about said hinge means.

7. A catheter grip as claimed in claim 1, wherein at least one of said first and second members is provided with a locating pin, and the other of said first and second members is provided with means defining a corresponding hole in which said locating pin is adapted to fit when said members are correctly closed together.

8. A catheter insertion pack containing a hollow needle, a Seldinger wire insertable through said needle, a vessel dilator insertable over said wire, a peel sheath insertable over said vessel dilator, a catheter insertable through said peel sheath, and a catheter grip as claimed in claim 1.

* * * * *